United States Patent [19]

Ricci

[11] 4,279,999
[45] Jul. 21, 1981

[54] MEANS FOR ACCELERATING PRECIPITATION IN IMMUNOASSAY AND IMMUNOASSAY METHOD

[75] Inventor: Giorgio Ricci, Rome, Italy

[73] Assignee: Biodata S.p.A., Italy

[21] Appl. No.: 926,703

[22] Filed: Jul. 20, 1978

[30] Foreign Application Priority Data

Jul. 27, 1977 [IT] Italy ................................. 50459 A/77

[51] Int. Cl.$^3$ ........................ C12N 9/00; G01N 33/54
[52] U.S. Cl. .................................. 435/183; 23/230 B; 424/1; 424/12; 435/7; 435/212; 252/408

[58] Field of Search ........................... 435/7, 212, 217; 23/230 B; 424/12, 1; 252/408; 260/112 B

[56] References Cited

U.S. PATENT DOCUMENTS 4,162,895  7/1979  Cambiaso et al. ................. 424/12 X Primary Examiner—Lionel M. Shapiro
Attorney, Agent, or Firm—Ostrolenk, Faber, Gerb & Soffen

[57] ABSTRACT

A serum factor extracted through dialysis of an animal serum or anti-serum has been found to accelerate precipitation in radioimmunoassays.

3 Claims, No Drawings

MEANS FOR ACCELERATING PRECIPITATION IN IMMUNOASSAY AND IMMUNOASSAY METHOD

This invention relates to the radioimmunological field. More particularly, this invention concerns immunological analysis and, still more particularly, a means for accelerating precipitation reactions in immunoassay and the relevant immunoassay method.

Radioimmunoassay (RIA) is an analytical technique permitting infinitesimal amounts of hormones or other substances which are present in biological fluids to be assayed.

Even though this technique is very precise and sensitive, it suffers from several disadvantages, for instance in that it requires rather lengthy operational times. For example, in one of the basic operations in RIA, such as, the separation of the immunocomplex (antigen-I-Antibody) from the excess free antigen, a precipitation reaction of the immunocomplex is commonly carried out which requires periods of about 24 hours. This kind of reaction occurs by addition of a second antibody (anti-gammaglobulin serum) to the incubation medium where the immunocomplex is found, and renders it precipitable as it forms a new antigen-I antibody-II antibody insoluble complex.

One main purpose of this invention is that of shortening the operational times for immunoassay by reducing the precipitation time of the immunocomplex.

Another object of this invention is a means of accelerating the insolubilization reaction and, therefore, the precipitation of the immunocomplex in radioimmunoassay.

Still another purpose of this invention is the relevant immunoassay method in which the new means for accelerating the precipitation is used. One further object of this invention is a process for preparing (that is, extracting) the above quoted accelerating means. Other objects and purposes of this invention will be understood from the following specification and examples.

As is known, the precipitation reaction of the immunocomplex is influenced by several elements such as:
(a) the quality of the anti-gammaglobulin serum;
(b) the temperature of reaction
(c) the volume of reaction
(d) pH and protein concentration of the incubation medium
(e) the presence of certain amount of salts in the reaction medium
(f) the gamma-globulin concentration of the animal species in which the I antibody was raised.

In the experiments which lead to this invention, the following operational conditions were used, which are listed below according to the same listing of the several factors mentioned above.
(a) a specific antiserum for gamma-globulin of the animal species in which the first antibody was raised is employed having a preestablished antibody titer and pre-established affinity for gamma-globulin.
(b) all reactions are performed at 20°–22° C.
(c) all reactions are performed in a final reaction volume of 0.4 milliliters.
(d) all reactions are performed at pH 7.5 and at a protein concentration of 3.3 mg/ml of bovine serum albumin.
(e) the following salts are present in the incubation medium:
0.01 molar phosphates
the sodium salt of ethylene diaminotetracetic acid (12.5 mg/ml)
(f) the gamma-globulin concentration is 16 ug per ml of the first anti-serum.

Among all these factors whose standardization is necessary in order that the precipitation reaction is carried out, there is none permitting the reaction to be accelerated.

This invention is based on the discovery that a "serum factor" exists which, when added to the incubation medium, has the property of accelerating the precipitation reaction. This serum factor (which has enzymatic activity) was found to be present in sera and antisera of numerous animal species such as man, rabbit, sheep, guinea-pig, and horse.

The extraction of the above mentioned serum factor from serum is accomplished by means of a dialysis procedure. The dialysis procedure is carried out as follows:

20 milliliters of human serum are placed in a dialyzing tube (Visking Tubing 24/32). The tube is accurately sealed and placed in a two liter beaker full of distilled water and left for 20 hours to dialyze, the distilled water being maintained constantly stirred. After 20 hours, the contents are centrifuged at approximately 2000 g. The supernatant is discarded and the solid matter (serum factor) is washed with distilled water, redissolved in 0.05 phosphate buffer and then lyophilized.

The so obtained serum factor is a protein having the aspect of a white powder and having the following chemical-physical characteristics:
(1) has a molecular weight higher than 50000 (Sephadex G-100)
(2) is the Euglobulin type, completely insoluble in distilled water
(3) has an electrophoretic mobility which is exactly the same as that of serum alpha or beta globulins.
(4) cannot be assimilated to any component of the serum complement
(5) is homogeneous on Sephadex G-100
(6) has enzymatic activity
(7) is thermolabile, that is, loses 90% of its activity when heated to 60° C. for 30 minutes.

The accelerating effect determined by the serum factor on the precipitation reaction is a phenomenon depending upon the concentration of the serum factor in the reaction medium. In fact, the amount of serum factor expressed in mg or in equivalent ml of serum to be added to the incubate, depends on how much the precipitation reaction is to be accelerated.

Sometimes, an accelerating effect can be obtained even using untreated serum. In this case, however, other side reactions may intervene in the assay making the use of untreated serum undesirable.

EXAMPLES

The following examples were carried out using RIA for determining human follicle-stimulating hormone (hFSH). Alternatively, other RIA models could be used to give similar results.

What follows is the general outline of examples 1(a), 1(b), 1(c) and 1(d).

To get formation of the immunocomplex (first reaction), the operational scheme followed was that explained below: 0.2 ml of anti-hFSH raised in rabbit and diluted 1:200,000 were reacted with 0.1 ml, equivalent to 0.08 nanograms, of I-125 labeled human FSH (specific radioactivity 150 microcurie per microgram). Once the equilibrium was reached (after 24 hours), the immunocomplex anti-hFSH-I-125-hFSH was made insoluble by adding to the reaction medium 0.1 ml of rabbit anti-gamma-globulin serum raised in sheep and diluted 1:300 (precipitating anti-serum). This operation was carried out in the following four different ways for the purpose of giving clear examples of this invention.

Example 1(a): Conventional way. At the end of the first reaction, only 0.1 ml of the precipitating anti-serum were added. Maximum precipitation was obtained after 24 hours reaction.

Example 1(b): According to this invention. At the end of the first reaction, serum factor in an amount equivalent to 0.01 ml human serum was added in addition to the precipitating anti-serum. Maximum precipitation was reached after 15 hours reaction.

Example 1(c): According to this invention. At the end of the first reaction, serum factor in an amount equivalent to 0.05 ml human serum was added in addition to the precipitating anti-serum. Maximum precipitation was obtained after 4 hours reaction.

Example 1(d): According to this invention. At the end of the first reaction, serum factor in an amount equivalent to 0.10 ml human serum was added in addition to the precipitating anti-serum.

Maximum precipitation was obtained after one hour reaction.

Analogous results were obtained using a serum factor raised in other animal species, such as those listed above.

In addition, it has been experimentally noticed that the precipitation reaction of the immunocomplex is accelerated even when the serum factor is added to the reaction medium containing the immunocomplex, before the said first reaction has reached equilibrium. It is well understood that the above described examples should not be considered limitative, but illustrative, of the invention, possible modifications being comprised in the wide ambit thereof.

I claim:

1. A serum free serum factor capable of accelerating precipitation during radioimmunoassay having the following chemical-physical characteristics:
    (a) a molecular weight higher than 50,000,
    (b) being of the Euglobulin type completely insoluble in distilled water,
    (c) having an electrophoretic mobility which is the same as serum alpha or beta globulins,
    (d) not assimilated to any component of the serum complement,
    (e) homogeneous on Sephadex G-100,
    (f) extracted by dialysis from animal serum or anti-serum, and
    (g) being thermolabile.

2. The serum factor of claim 1 in lyophilized form.

3. Process for obtaining the serum factor claimed in claim 1 comprising dialyzing animal serum or anti-serum against constantly stirred distilled water thereby recovering said serum factor by extraction, centrifuging and washing the solid with distilled water, redissolving in a buffer and then lyophilizing to thereby obtain the lyophilized serum factor.

* * * * *